United States Patent [19]

Bahrmann

[11] Patent Number: 5,741,941
[45] Date of Patent: Apr. 21, 1998

[54] PROCESS FOR PREPARING ALDEHYDES

[75] Inventor: Helmut Bahrmann, Hamminkeln, Germany

[73] Assignee: Hoechst Aktiengesellschaft, Germany

[21] Appl. No.: 811,825

[22] Filed: Mar. 5, 1997

[30] Foreign Application Priority Data

Mar. 20, 1996 [DE] Germany .................. 196 10 869.1

[51] Int. Cl.$^6$ .................................................. C07C 45/50
[52] U.S. Cl. ......................................................... 568/451
[58] Field of Search ................................. 568/451, 429

[56] References Cited

U.S. PATENT DOCUMENTS 5,091,350  2/1992  Cornils .

FOREIGN PATENT DOCUMENTS 0491239  6/1992  European Pat. Off. .
0571819  12/1993  European Pat. Off. .
0602442  6/1994  European Pat. Off. .
0602463  6/1994  European Pat. Off. .

OTHER PUBLICATIONS

CA:117:150499, Abs of "Water soluble metal complexes and catalysts", Herrmann, J Mol Cat. 73(2), 1992.
CA 123:144025, Abs of "Water soluble metal complexes and catalysts", Herrman, J Mol Cat. 97(2), 1995.

Primary Examiner—Gary Geist
Assistant Examiner—Jean F. Vollano
Attorney, Agent, or Firm—Bierman, Muserlian and Lucas

[57] ABSTRACT

A process for preparing aldehydes by reacting straight-chain or branched olefins of at least 4 carbon atoms with carbon monoxide and hydrogen in the liquid phase in the presence of water, solubilizers and a catalyst system comprising water-soluble rhodium complexes, wherein the rhodium complexes present in the catalyst system contain specific sulfonated diphosphines as ligands and the solubilizers are quaternary ammonium salts.

16 Claims, No Drawings

PROCESS FOR PREPARING ALDEHYDES

The present invention relates to a process for preparing aldehydes by hydroformylation of higher olefins in the presence of water-soluble rhodium complex catalysts and solubilizers.

BACKGROUND OF THE INVENTION

It is known that aldehydes and alcohols can be prepared by reacting olefins with carbon monoxide and hydrogen. The hydroformylation is catalyzed by hydrido-metal carbonyls, preferably those of metals of group VIII of the Periodic Table. Apart from cobalt which is widely used in industry as a catalyst metal, rhodium has recently been gaining increasing importance. In contrast to cobalt, rhodium allows the reaction to be carried out at low pressure and, in addition, straight-chain-n-aldehydes are preferentially formed and iso-aldehydes are formed only to a lesser extent. Finally, the hydrogenation of the olefins to obtain saturated hydrocarbons is significantly less pronounced when using rhodium catalysts than when using cobalt catalysts.

In the processes which have been introduced in industry, the rhodium catalyst is used in the form of modified hydridorhodium carbonyls which additionally contain ligands. The ligands are usually present in excess so that the catalyst system comprises the rhodium complex and free ligand. Ligands which have been found to be particularly useful are tertiary phosphines or phosphites. Their use makes it possible to lower the reaction pressure in the hydroformylation to values of less than 30 MPa.

However, this process poses problems in the separation of the reaction products and the recovery of the catalysts which are homogeneously dissolved in the reaction product. In general, this is achieved by distilling off the reaction product from the reaction mixture. However, because of the thermal sensitivity of the aldehydes and alcohols formed, this method can be used in practice only in the hydroformylation of lower olefins, i.e. olefins having up to about 6 carbon atoms in the molecule. In addition, it has been found that the thermal stressing of the material being distilled also leads to considerable catalyst losses as a result of decomposition of the rhodium complexes.

The deficiencies indicated are avoided by using catalyst systems which are soluble in water and such catalyst systems are described, for example, in DE-C-26 27 354, EP-A-0 571 819 and EP-B-0 491 240. The solubility of the rhodium complexes is achieved by use of sulfonated or carboxylated triarylphosphines or sulfonated diphosphines as constituents of the complex. In this process variant, the separation of the catalyst from the reaction product after the hydroformylation reaction is complete is carried out simply by separating the aqueous and organic phases, i.e. without distillation and thus without additional, thermal process steps.

This hydroformylation using water-soluble catalyst systems has been found to be very useful for the lower olefins, i.e. ethylene, propylene and the butenes. If higher olefins such as hexene, octene or decene are used, the conversion in the hydroformylation drops noticeably so that the reaction is no longer economical on an industrial scale. The drop in the conversion is caused by the decrease in the solubility of higher olefins in water, since the reaction between the reactants proceeds in the aqueous phase.

EP-B-0 157 316 discloses carrying out the hydroformylation of higher olefins in the presence of an aqueous phase and an organic phase which is immiscible or only slightly miscible with the aqueous phase plus solubilizers. Catalysts used are rhodium complexes containing trisulfonated triaryl phosphines. The solubilizers are cationic phase transfer reagents of the formula

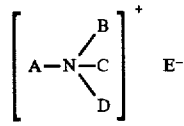

wherein A is a straight-chain or branched alkyl, ω-hydroxyalkyl, alkoxy or unsubstituted or substituted aryl, each having from 6 to 25 carbon atoms or is $R^7$—CONH—$CH_2$—$CH_2$—$CH_2$—, where $R^7$ is a straightchain or branched alkyl of 5 to 11 carbon atoms, B, C and D are individually straight-chain or branched alkyl or ω-hydroxyalkyl of 1 to 4 carbon atoms or C and D together with N form a heterocyclic five- or six-membered ring and E is chloride, bromide, iodide or preferably sulfate, tetrafluoroborate, acetate, methosulfate, benzene sulfonate, alkylbenzene sulfonate, toluene sulfonate, lactate or citrate.

In the hydroformylation of n-hex-1-ene in the presence of these solubilizers, conversion increases from about 20% to an average of 40% are achieved in comparison with the hydroformylation without solubilizers. However, in the presence of the solubilizer, the ratio of n-aldehyde to the iso-aldehydes at the same time worsens from 98:2 (without solubilizer) to from 95:5 to 96:4.

However, a conversion level of about 40% is too low for industrial use. Optimization of the reaction conditions in the form of a reduction of the amounts of solubilizer added can increase the conversion from 40% to 70–75%, but at the same time the n/i ratio drops still further to 91:9. From an economic point of view, this value is totally unsatisfactory with regard to the yield of desired n-aldehyde.

OBJECTS OF THE INVENTION

It is an object of the invention to develop a process which allows higher olefins to be hydroformylated in a multiphase system composed of aqueous catalyst solution and organic starting materials and optionally reaction products and gaseous reactants to give n-aldehydes with a high conversion and simultaneously in high selectivity.

This and other objects and advantages of the invention will become obvious from the following detailed description.

THE INVENTION

The novel process of the invention for the preparation of aldehydes comprises reacting olefinically unsaturated compounds of at least 3 carbon atoms with carbon monoxide and hydrogen in the liquid phase in the presence of water, solubilizers and a catalyst system comprising water-soluble rhodium complexes, wherein the water-soluble rhodium complexes present in the catalyst system contain as ligands diphosphines of the formula

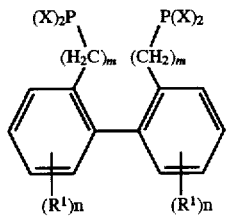

I substituted by at least one sulfonic acid, wherein the Xs are individually selected from the group consisting of alkyl of 1 to 9 carbon atoms, cycloalkyl of 6 to 10 carbon atoms, substituted or unsubstituted aryl of 6 to 10 carbon atoms and biaryl of 12 carbon atoms, $R^1$s are individually selected from the group consisting of hydrogen, alkyl of 1 to 14 carbon atoms, alkoxy of 1 to 14 carbon atoms, cycloalkyl of 6 to 14 carbon atoms, aryl of 6 to 14 carbon atoms, aryloxy of 6 to 14 carbon atoms and a fused-on benzene ring, ms are individually an integer from 0 to 5 and ns are individually integers from 0 to 4, and the solubilizers used are compounds of the formula

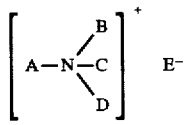

II wherein A is a straight-chain or branched alkyl of 6 to 25 carbon atoms, ω-hydroxyalkyl of 6 to 25 carbon atoms, substituted or unsubstituted aryl of 6 to 25 carbon atoms and $R^7$—CONH—$CH_2$—$CH_2$—$CH_2$—, wherein $R^7$ is a straight-chain or branched alkyl of 5 to 11 carbon atoms, B, C and D are individually straight-chain or branched alkyl or ω-hydroxyalkyl of 1 to 4 carbon atoms or C and D together with N form a five- or six-membered heterocyclic ring and $E^-$ is an inorganic or organic anion.

The hydroformylation of olefins occurs in the presence of sulfonated diphosphines of formula I as constituent of the rhodium complex and said solubilizers of formula II to give n-aldehydes with long-term high conversion and a high degree of selectivity.

In formula I, X is preferably phenyl, tolyl or naphthyl, $R^1$ is preferably hydrogen or methyl, isopropyl, isobutyl, t-butyl, phenyl or naphthyl or a fused-on benzene ring, m is preferably 1 and n is preferably 0 or 1.

$E^-$ in formula I is an inorganic anion, preferably a halide ion, or sulfate, methosulfate, sulfonate or borate ion. $E^-$ is preferably chloride, bromide, iodide, benzene sulfonate, $C_7$–$C_{10}$-alkylbenzene-sulfonate, particularly toluene sulfonate or tetrafluoroborate.

$E^-$ in formula I may also be an organic anion, preferably a carboxylate, lactate or citrate ion. Most preferred is the acetate ion.

Particularly useful ligands for the water-soluble rhodium complexes have been found to be the sulfonated 2,2'-bis (diphenylphosphinomethyl)-1,1'-binaphthyls derived from formula I and having the formula

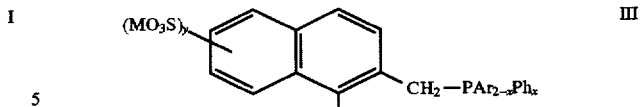

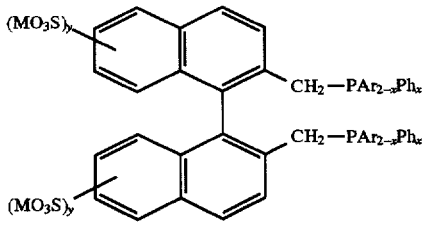

III wherein Ar is m-$C_6H_4SO_3M$, M is hydrogen, ammonium, a monovalent metal or the equivalent of a polyvalent metal, preferably lithium, sodium, potassium or barium, and Ph is phenyl, ys are individually 1 or 2, preferably 2, and xs are individually 0, 1 or 2, preferably 1 or 2.

The sulfonated diphosphines of formulae II and III are prepared by the methods known to one skilled in the art such as the process of EP-B-0 491 240 and EP-A-0 571 819.

The solubilizers of formula II are materials which are compatible with both the aqueous and the organic phase and, particularly at elevated temperatures, are soluble in both phases. Such materials are known and are also referred to as phase transfer reagents, surface-active reagents or amphiphilic reagents or as surfactants. Their effect is primarily to change the physical properties of the interfaces between the two liquid phases and thereby to aid the transfer of the organic reactant into the aqueous catalyst phase. It is particularly important in this context that the solubilizer has no adverse influence on the activity of the catalytically active metal.

The solubilizers of formula II which are used belong to the class of cationic phase transfer reagents, wherein A is a straight-chain or branched alkyl of 6 to 25 carbon atoms, preferably 8 to 20 carbon atoms and more preferably 10 to 16 carbon atoms, ω-hydroxyalkyl of 6 to 25 carbon atoms, preferably 8 to 20 carbon atoms and more preferably 10 to 18 carbon atoms, alkoxy of 6 to 25 carbon atoms, preferably 8 to 20 carbon atoms and more preferably 10 to 16 carbon atoms, or a substituted or unsubstituted aryl of 6 to 25 carbon atoms, preferably 6 to 18 carbon atoms and most preferably 6 to 12 carbon atoms or $R^7$—CONH—$CH_2$—$CH_2$—$CH_2$—, wherein $R^7$ is a straight-chain or branched alkyl radical of 5 to 11, preferably from 4 to 10, more preferably from 3 to 9, carbon atoms, B, C and D are individually straight-chain or branched alkyl or ω-hydroxyalkyl of 1 to 4, preferably 2 or 3 carbon atoms or C and D together with N form a six-membered heterocyclic ring.

Examples of suitable cations [NABCD]$^+$ are stearyltrimethylammonium, phenyltrimethylammonium, trimethyl-1-phenylammonium, benzyltrimethylammonium, cetyltrimethylammonium, myristyltrimethylammonium, dodecylpyridinium, stearylamidomethylpyridinium, lauryltrimethylammonium, benzyltriethylammonium, N-(3-trimethylammoniumpropyl)-n-heptanamide, dodecyltris-β-hydroxyethylammonium and N-(β-trimethylammoniumpropyl)-N-nonanamide.

Anions $E^-$ which can be used in formula II are chloride, bromide, iodide, sulfate, tetrafluoroborate, acetate, methosulfate, benzene sulfonate, alkylbenzene sulfonate, toluene sulfonate, lactate or citrate. Owing to their low corrosiveness, preference is given to methosulfates, sulfonates and lactates.

The concentration of the solubilizers in the aqueous catalyst solution is from 0.05 to 5% by weight, preferably 0.07–2% by weight and more preferably 0.1–0.5% by weight, based on the catalyst solution.

The catalyst can be preformed before addition to the reaction system. However, it can be equally successfully prepared from the components of rhodium or rhodium compound and the aqueous solution of the diphosphine of formula I in the reaction mixture under the reaction conditions, i.e. in the presence of the olefin. Apart from metallic rhodium in finely divided form, sources of rhodium which can be used are water-soluble rhodium salts such as rhodium chloride, rhodium sulfate, rhodium acetate or compounds soluble in organic media, e.g. rhodium 2-ethylhexanoate, or insoluble compounds such as rhodium oxides.

The rhodium concentration in the aqueous catalyst solution is from 10 to 2000 ppm by weight, preferably 20–300 ppm by weight and more preferably 40–100 ppm by weight, based on the catalyst solution. The diphosphine is used in such an amount that from 1 to 50 mol, preferably from 5 to 15 mol, of the diphosphine are present per 1 mol of rhodium.

The pH of the aqueous catalyst solution should not be below 2 and the pH employed is generally from 2 to 13, preferably from 4 to 10.

The reaction of the olefin with hydrogen and carbon monoxide is carried out at temperatures of 20° to 150° C. preferably 50° to 120° C., and pressures of 0.1 to 20 MPa, preferably 1 to 10 MPa.

The composition of the synthesis gas, i.e. the ratio of carbon monoxide to hydrogen, can be varied within wide limits. Use is generally made of a synthesis gas in which the volume ratio of carbon monoxide to hydrogen is 1:1 or is only slightly different from this value. The reaction can be carried out either continuously or batchwise.

The process of the invention is successfully employed in the hydroformylation of olefinically unsaturated compounds having at least 3 carbon atoms. Particularly suitable substrates are olefinically unsaturated compounds having from 3 to 20 carbon atoms which can have one or more, internal and/or terminal double bonds. Suitable olefinically unsaturated compounds are substituted or unsubstituted alkenes of 3 to 20 carbon atoms, substituted or unsubstituted dienes of 4 to 10 carbon atoms, substituted or unsubstituted cycloalkenes or dicycloalkenes of 5 to 12 carbon atoms in the ring system, esters of an unsaturated carboxylic acid of 3 to 20 carbon atoms and an aliphatic alcohol of 1 to 18 carbon atoms, esters of a saturated carboxylic acid of 2 to 20 carbon atoms and unsaturated alcohol of 2 to 18 carbon atoms, unsaturated alcohols or ethers of 3 to 20 carbon atoms or araliphatic olefins of 8 to 20 carbon atoms.

The substituted or unsubstituted alkenes of 3 to 20 carbon atoms may be straight-chain or branched alkenes having the double bond in a terminal or internal position. Preference is given to straight-chain olefins of 6 to 18 carbon atoms such as n-hex-1-ene, n-hept-1-ene, n-oct-1-ene, n-non-1-ene, n-dec-1-ene, n-undec-1-ene, n-dodec-1-ene, n-octodec-1-ene and acyclic terpenes. Also suitable are branched alkenes such as diisobutylene (2,4,4-trimethylpent-1-ene), tripropylene, tetrapropylene and dimersol.

Preferred examples of unsubstituted dienes of 4 to 10 carbon atoms are 1,3-butadiene, 1,5-hexadiene and 1,9-decadiene. Examples of substituted and unsubstituted cycloalkenes or dicycloalkenes of 5 to 12 carbon atoms in the ring system are cyclohexene, cyclooctene, cyclooctadiene, dicyclopentadiene and cyclic terpenes such as limonene, pinene, camphorene and bisabolene. An example of an araliphatic olefin of 8 to 20 carbon atoms is styrene.

Examples of esters of an unsaturated carboxylic acid of 3 to 20 carbon atoms and an aliphatic alcohol of 1 to 18 carbon atoms are acrylic and methacrylic esters of 1 to 18 carbon atoms in the alcohol component. Esters of a saturated carboxylic acid of 2 to 20 carbon atoms and an unsaturated alcohol of 2 to 18 carbon atoms include vinyl and allyl esters of 2 to 20 carbon atoms in the carboxylic acid component. The unsaturated alcohols and ethers include, for example, allyl alcohols and vinyl ethers.

In the examples below, the performance of the catalyst systems is described by, apart from the ratio of n-aldehyde to i-aldehyde, the terms "activity" defined as $$\frac{\text{mol of aldehydes}}{\text{g-atom of Rh} \cdot \text{min}}$$

and "productivity" defined as $$\frac{\text{g of aldehydes}}{\text{cm}^3 \text{ of catalyst solution} \cdot \text{h}}.$$

Alcohol and hydrocarbon formation is minimal.

In the following examples, there are described several preferred embodiments to illustrate the invention. However, it should be understood that the invention is not intended to be limited to the specific embodiments.

EXAMPLES 1–3

(Comparison; complexing ligand: trisodium tri(m-sulfophenyl)phosphine (TPPTS); addition of solubilizier)

a) Preformation of the catalyst

A 1 liter autoclave fitted with an immersed tube was charged with 450 g (419 ml) of an aqueous solution of TPPTS containing 16.4% by weight of salt plus 300 ppm of Rhas rhodium acetate. In addition, 75.3 g of tetradecyltrimethylammonium TPPTS solution (5.1% strength) corresponding to 3.86 g of 100% pure salt, corresponding to 0.86% of the total TPPTS solution, were added. The autoclave was then pressurized with a synthesis gas (CO/H$_2$ volume ratio=1:1) to a pressure of 2.5 MPa. The reaction solution was then treated with synthesis gas for 3 hours while stirring at 125° C., with the active catalyst being formed. After cooling to about 30° C., the stirrer was switched off and, after a settling time of 15 minutes, the excess solution was discharged under pressure through the immersed tube and analyzed. The rest of the solution remained in the autoclave.

b) Hydroformylation 105 g of n-hex-1-ene were pumped into the solution prepared as described in a) with stirring at a constant pressure of 2.5 MPa and the mixture was heated to 125° C. and left for 3 hours at this temperature. The mixture was cooled to 30° C. and allowed to settle. The supernatant organic phase was discharged under pressure through the immersed tube and it was weighed (see Table 1) and analyzed by gas chromatography. The substep b) was repeated twice, with essentially the same results being obtained. The values shown for activity and productivity in Table 1 are based on the amounts of aqueous and organic phase present in the autoclave. The amount of hexene used was matched to the level in the autoclave.

TABLE 1

| Examples | 1 | 2 | 3 | mean |
|---|---|---|---|---|
| n-hex-1-ene used (g) | 104 | 103 | 98 | 100.5 |
| conversion (% by GC) | 75 | 72 | 74 | 73 |
| n/i ratio | 91/9 | 91/9 | 91/9 | 91/9 |
| organic phase (g) | 123.3 | 122.1 | 118 | 119.4 |
| aqueous phase in the | 417 | 411 | 392 | 402.3 |

TABLE 1-continued

| Examples | 1 | 2 | 3 | mean |
|---|---|---|---|---|
| reactor (g) | | | | |
| activity (mol of $C_7$-al* (mol of Rh)$^{-1}$min$^{-1}$) | 3.62 | 3.49 | 3.44 | 3.50 |
| productivity (g of $C_7$-al* (cm$^3$ of cat.solution)$^{-1}$h$^{-1}$ | 0.079 | 0.076 | 0.075 | 0.076 |

EXAMPLES 4–6

(comparison, complexing ligand: sulfonated 2,2'-bis (diphenylphosphinomethyl)-1,1'-binaphthyl (BINAS), without addition of a solubilizer).

a) Preformation of the catalyst

A 0.2 liter autoclave fitted with an immersed tube was charged with 109 ml (110 g) of an aqueous solution of BINAS plus 50 ppm of Rh as rhodium acetate. The autoclave was then pressurized with a synthesis gas (CO/H$_2$ volume ratio=1:1) to a pressure of 2.5 MPa and the reaction solution was treated with synthesis gas for 3 hours with stirring at 122° C., with the active catalyst being formed. After cooling to about 30° C., the stirrer was switched off and, after a settling time of 15 minutes, the excess solution was discharged under pressure through the immersed tube and analyzed. The rest of the solution remained in the autoclave.

b) Hydroformylation 34.3 g of n-hex-1-ene were pumped into the solution prepared as described in a) with stirring and at a constant pressure of 2.5 MPa, the mixture was heated to 122° C. and left for 3 hours at this temperature. After the mixture cooled to 30° C. and allowed to settle, the supernatant organic phase was discharged under pressure through the immersed tube. It was weighed and analyzed by gas chromatography.

The substep b) was repeated twice, with essentially the same results being obtained. The values shown for activity and productivity in Table 2 are based on the amounts of aqueous and organic phase present in the autoclave. The amount of n-hex-1-ene used was matched to the level in the autoclave.

TABLE 2

| Examples | 4 | 5 | 6 | mean |
|---|---|---|---|---|
| n-hex-1-ene used (g) | 34.3 | 34.3 | 34.3 | 34.3 |
| conversion (% by GC) | 33 | 36 | 39 | 36 |
| n/i ratio | 97.3/2.7 | 99.1/0.9 | 99.1/0.9 | 98.5–1.5 |
| organic phase (g) | 32.0 | 38.4 | 36.9 | 35.8 |
| aqueous phase in the reactor (g) | 68.5 | 68.5 | 68.5 | 68.5 |
| activity (mol of $C_7$-al* (mol of Rh)$^{-1}$min$^{-1}$) | 15.2 | 20.1 | 21.3 | 18.9 |
| productivity (g of $C_7$-al* (cm$^3$ of cat.solution)$^{-1}$h$^{-1}$ | 0.049 | 0.065 | 0.069 | 0.061 |

EXAMPLES 7–9

(complexing ligand: BINAS, addition of a solubilizer)

a) Preformation of the catalyst

A 0.2 liter autoclave fitted with an immersed tube was charged with 112 g of an aqueous solution of BINAS plus 50 ppm of Rh as rhodium acetate. In addition, 1 g of tetradecyltrimethylammonuium methocarbonate solution (27.2% strength) corresponding to 0.272 g of 100% pure salt, corresponding to 0.241% of the total BINAS solution, was added and the autoclave was then pressurized with a synthesis gas (CO/H$_2$ volume ratio=1:1) to a pressure of 2.5 MPa. The reaction solution was treated with synthesis gas for 3 hours with stirring at 122° C., with the active catalyst being formed. After cooling to about 30° C., the stirrer was switched off and, after a settling time of 15 minutes, the excess solution was discharged under pressure through the immersed tube and analyzed. The rest of the solution remained in the autoclave.

b) Hydroformylation 36.7 g of n-hex-1-ene were pumped into the solution prepared as described in a) with stirring and at a constant pressure of 25 bar (2.5×10$^3$ kPa), the mixture was heated to 122° C. and left for 3 hours at this temperature. After the mixture was cooled to 30° C. and allowed to settle, the supernatant organic phase was discharged under pressure through the immersed tube. It was weighed and analyzed by gas chromatography. The substep b) was repeated twice, with essentially the same results being obtained. The values shown for activity and productivity in Table 3 are based on the amounts of aqueous and organic phase present in the autoclave. The amount of hexene used was matched to the level in the autoclave.

TABLE 3

| Examples | 7 | 8 | 9 | mean |
|---|---|---|---|---|
| n-hex-1-ene used (g) | 36.5 | 36.5 | 36.5 | 36.5 |
| conversion (% by GC) | 79 | 76 | 77 | 77.3 |
| n/i ratio | 99/1 | 99/1 | 99/1 | 99/1 |
| organic phase (g) | 37 | 46 | 44 | 42.3 |
| aqueous phase in the reactor (g) | 73.4 | 73.4 | 73.0 | 73.3 |
| activity (mol of $C_7$-al* (mol of Rh)$^{-1}$min$^{-1}$) | 37.3 | 44.1 | 43.9 | 41.8 |
| productivity (g of $C_7$-al* (cm$^3$ of cat.solution)$^{-1}$h$^{-1}$ | 0.130 | 0.154 | 0.153 | 0.146 |

Examples 7–9 show that, when using BINAS as a complexing ligand, the addition of the solubilizer significantly increases conversion, activity and productivity, and at the same time the selectivity is just as high as without addition of a solubilizer.

EXAMPLES 10–12

These examples were carried out using a method similar to Examples 7–9, but the preformation of the catalyst was carried out at 110° C. and the reaction time in the hydroformylation was doubled from 3 hours to 6 hours. The results of the hydroformylation are shown in Table 4.

TABLE 4

| Examples | 10 | 11 | 12 | mean |
|---|---|---|---|---|
| n-hex-1-ene used (g) | 35 | 35 | 35 | 35 |
| conversion (% by GC) | 85.7 | 84.5 | 82.3 | 84.2 |
| n/i ratio | 99/1 | 99/1 | 98/2 | 99/1 |
| organic phase (g) | 38.2 | 43.0 | 41.1 | 40.8 |
| aqueous phase in the reactor (g) | 69.0 | 69.0 | 68.0 | 68.7 |
| activity (mol of $C_7$-al* (mol of Rh)$^{-1}$min$^{-1}$) | 22.81 | 24.71 | 16.17 | 21.23 |
| productivity | 0.076 | 0.082 | 0.054 | 0.071 |

TABLE 4-continued

| Examples | 10 | 11 | 12 | mean |
| --- | --- | --- | --- | --- |
| (g of C$_7$-al* (cm$^3$ of cat.solution)$^{-1}$h$^{-1}$ | | | | |

Examples 10–12 show that, when using a solubilizer in the presence of BINAS as complexing ligand, varying the reaction conditions, in particular prolonging the hydroformylation time, can significantly further increase the conversion while the n/i ratio remains excellent.

Various modifications of the process of the invention may be made without departing from the spirit or scope thereof and it is to be understood that the invention is intended to be limited only as defined in the appended claims.

What I claim is:

1. A process for preparing aldehydes comprising reacting olefinically unsaturated compounds of at least 3 carbon atoms with carbon monoxide and hydrogen in the liquid phase in the presence of water, solubilizers and a catalyst system comprising water-soluble rhodium complexes, wherein the water-soluble rhodium complexes present in the catalyst system contain as ligands diphosphines of the formula

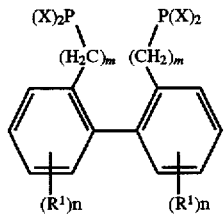

substituted by at least one sulfonic acid, wherein the Xs are individually selected from the group consisting of alkyl of 1 to 9 carbon atoms, cycloalkyl of 6 to 10 carbon atoms, substituted or unsubstituted aryl of 6 to 10 carbon atoms and biaryl of 12 carbon atoms, R$^1$s are individually selected from the group consisting of hydrogen, alkyl of 1 to 14 carbon atoms, alkoxy of 1 to 14 carbon atoms, cycloalkyl of 6 to 14 carbon atoms, aryl of 6 to 14 carbon atoms, aryloxy of 6 to 14 carbon atoms and a fused-on benzene ring, ms are individually an integer from 0 to 5 and ns are individually integers from 0 to 4, and the solubilizers used are compounds of the formula

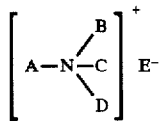

wherein A is a straight-chain or branched alkyl of 6 to 25 carbon atoms, ω-hydroxyalkyl of 6 to 25 carbon atoms, substituted or unsubstituted aryl of 6 to 25 carbon atoms and R$^7$—CONH—CH$_2$—CH$_2$—CH$_2$—, wherein R$^7$ is a straight-chain or branched alkyl of 5 to 11 carbon atoms, B, C and D are individually straight-chain or branched alkyl or ω-hydroxyalkyl of 1 to 4 carbon atoms or C and D together with N form a five- or six-membered heterocyclic ring and E$^-$ is an inorganic or organic anion.

2. The process of claim 1, wherein Xs are individually selected from the group consisting of phenyl, tolyl and naphthyl and R$^1$s are individually selected from the group consisting of hydrogen, methyl, isopropyl, isobutyl, t-butyl, phenyl and naphthyl, m is 1 and n is 0 or 1.

3. The process of claim 1 wherein A is selected from the group consisting of alkyl of 8 to 20 carbon atoms, ω-hydroxyalkyl of 8 to 20 carbon atoms, optionally substituted aryl of 6 to 18 carbon atoms and R$^7$—CONH—CH$_2$—CH$_2$—CH$_2$—, R$^7$ is alkyl of 4 to 10 carbon atoms, B, C and D are individually alkyl or ω-hydroxyalkyl of 2 to 3 carbon atoms or C and D together with the nitrogen form a six-membered heterocyclic ring.

4. The process of claim 1 wherein E$^-$ is selected from the group consisting of halide, sulfate, methosulfate, sulfonate and borate ions.

5. The process of claim 4 wherein E$^-$ is selected from the group consisting of chloride, bromide, iodide, benzene sulfonate, alkylbenzene sulfonate of 7 to 10 carbon atoms and tetrafluoroborate.

6. The process of claim 1 wherein E$^-$ is a carboxylate ion.

7. The process of claim 6 wherein the carboxylate ion is selected from the group consisting of acetate ion, lactate ion and citrate ion.

8. The process of claim 1 wherein the ligands of the water-soluble rhodium complexes are sulfonated 2,2'-bis (diphenylphosphinomethyl)-1,1'-binaphthyls of the formula

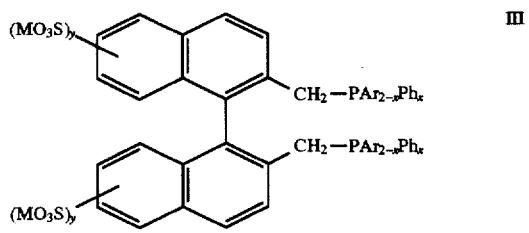

wherein Ar is m-C$_6$H$_4$—SO$_3$M, M is selected from the group consisting of hydrogen, ammonia, monovalent metal and equivalent of polyvalent metal, Ph is phenyl, ys are individually 1 or 2 and xs are individually 0, 1 or 2.

9. The process of claim 8 wherein M is selected from the group consisting of lithium, sodium, potassium and barium, ys are 2 and xs are individually 1 or 2.

10. The process of claim 1 wherein the solubilizer concentration in the aqueous catalyst solution is 0.05 to 5% by weight, based on the catalyst solution.

11. The process of claim 10 wherein the solubilizer concentration is 0.1 to 0.5%.

12. The process of claim 1 wherein the rhodium concentration in the aqueous catalyst system is 10 to 2000 ppm by weight, based on the catalyst system and 1 to 5 mol of diphosphine is used per mol of rhodium.

13. The process of claim 12 wherein the rhodium concentration is 40 to 100 ppm by weight and 5 to 15 mols of disphosphine are used per mol of rhodium.

14. The process of claim 1 wherein the process is effected at 20° to 150° C. and a pressure of 0.1 to 20 MPa.

15. The process of claim 14 wherein the process is effected at 50° to 120° C. and a pressure of 1 to 10 MPa.

16. The process of claim 1 wherein the olefinically unsaturated compounds are selected from the group consisting of optionally substituted alkenes of 3 to 20 carbon atoms, optionally substituted dienes of 4 to 10 carbon atoms, optionally substituted cycloalkenes and dicycloalkenes of 5 to 12 ring carbon atoms, esters of an unsaturated carboxylic acid of 3 to 20 carbon atoms and an aliphatic alcohol of 1 to 18 carbon atoms, esters of a saturated carboxylic acid of 2 to 20 carbon atoms and an unsaturated alcohol of 2 to 18 carbon atoms, unsaturated alcohols and ethers of 3 to 20 carbon atoms and araliphatic olefins of 8 to 20 carbon atoms.

* * * * *